US007873480B2

(12) United States Patent
Rimm et al.

(10) Patent No.: US 7,873,480 B2
(45) Date of Patent: Jan. 18, 2011

(54) SYSTEMS AND METHODS FOR AUTOMATED ANALYSIS OF CELLS AND TISSUES

(75) Inventors: David L. Rimm, Branford, CT (US); Robert L Camp, Stamford, CT (US)

(73) Assignee: Yale University, New Haven, CT (US)

( * ) Notice: Subject to any disclaimer, the term of this patent is extended or adjusted under 35 U.S.C. 154(b) by 588 days.

(21) Appl. No.: 11/894,680

(22) Filed: Aug. 20, 2007

(65) Prior Publication Data

US 2008/0056553 A1 Mar. 6, 2008

Related U.S. Application Data

(60) Division of application No. 11/789,361, filed on Apr. 23, 2007, which is a continuation of application No. 10/062,308, filed on Feb. 1, 2002, now Pat. No. 7,219,016.

(60) Provisional application No. 60/334,723, filed on Oct. 31, 2001, provisional application No. 60/285,155, filed on Apr. 20, 2001.

(51) Int. Cl.
*G01N 33/48* (2006.01)
(52) U.S. Cl. ...................................... 702/19
(58) Field of Classification Search .................. 702/19
See application file for complete search history.

(56) References Cited

U.S. PATENT DOCUMENTS

| 4,998,284 | A | 3/1991 | Bacus et al. |
| 5,386,819 | A | 2/1995 | Kaneko et al. |
| 5,784,162 | A | 7/1998 | Cabib et al. |
| 5,989,835 | A | 11/1999 | Dunlay et al. |
| 5,998,151 | A | 12/1999 | Johnston et al. |
| 6,026,174 | A | 2/2000 | Palcic et al. |
| 6,151,405 | A | 11/2000 | Douglass et al. |
| 6,165,734 | A | 12/2000 | Garini et al. |
| 6,215,892 | B1 | 4/2001 | Douglass et al. |
| 6,229,649 | B1 | 5/2001 | Woods et al. |
| 6,251,601 | B1 | 6/2001 | Bao et al. |
| 6,337,472 | B1 | 1/2002 | Garner et al. |
| 6,466,690 | B2 | 10/2002 | Bacus et al. |
| 6,727,071 | B1 | 4/2004 | Dunlay et al. |
| 7,050,087 | B2 | 5/2006 | Harari et al. |
| 2003/0036855 | A1 | 2/2003 | Harris et al. |
| 2005/0227303 | A1 | 10/2005 | Guo et al. |
| 2006/0127928 | A1 | 6/2006 | Bacus et al. |
| 2006/0147959 | A1 | 7/2006 | Bell et al. |
| 2006/0275844 | A1 | 12/2006 | Linke et al. |
| 2008/0013816 | A1 | 1/2008 | Rimm et al. |
| 2008/0026415 | A1 | 1/2008 | Rimm et al. |
| 2008/0026420 | A1 | 1/2008 | Rimm et al. |
| 2008/0046190 | A1 | 2/2008 | Rimm et al. |
| 2009/0155767 | A1 | 6/2009 | Rimm et al. |

FOREIGN PATENT DOCUMENTS

| WO | WO 90/10276 | 9/1990 |
| WO | WO 97/04418 | 2/1997 |
| WO | WO 97/22848 | 6/1997 |
| WO | WO 99/47963 | 9/1999 |
| WO | 0024940 | 5/2000 |
| WO | WO 00/31534 | 6/2000 |
| WO | 0120044 | 9/2000 |
| WO | 0122086 | 9/2000 |
| WO | WO 00/62247 | 10/2000 |
| WO | WO/02/86498 | 4/2002 |
| WO | WO 2008/008500 | 1/2008 |
| WO | WO 2009/005715 | 1/2009 |
| WO | WO 2009/005816 | 1/2009 |

OTHER PUBLICATIONS

Arnold et al., "Molecular Determinants for Subcellular Localization of PSD-95 with an Interacting K+ Channel," *Neuron*, May 1999, 24:149-157.
Chen et al., "Ratio-Base Decisions and the Quantitative Analysis of cDNA Microarray Images," *J. Biomed. Optics*, Oct. 1997, 2(4):364-374.
Forus et al., "Sensitive Fluorescent in situ Hybridisation Method for the Characterisation of Breast Cancer Cells in Bone Marrow Aspirates," *The Journal of Clinical Pathology*, 1999, 52:68-74.
Klein et al., "The Neuroimmune Interface in Prion Diseases," *News Physiol. Sci.*, Oct. 2000, 15:250-255.
Rigaut et al., "Three-Dimensional DNA Image Cytometry by Confocal Scanning Laser Microscopy in Thick Tissue Blocks," *Cytometry*, 1991, 12:511-524.
Staines et al., "Three-Color Immunofluorescence Histochemistry Allowing Triple Labeling Within a Single Section," *The Journal of Histochemistry and Cytochemistry*, (1988), 36(6):145-151.
Wood et al., "B-Spectrin is Colocalized with Both Voltage-gated Sodium Channels and AnkyrinG at the Adult Rat Neuromuscular Junction," *The Journal of Cell Biology*, 1998, 140(3):675-684.
Zhon et al., "A Multiple Wavelength Algorithm in Color Image Analysis and Its Applications in Stain Decomposition in Microscopy Images," *Med. Phys.*, 1996, 23(12):1977-1986.
U.S. Appl. No. 12/661,141, filed Mar. 10, 2010, David L. Rimm et al.
International Search Report issued by the International Searching Authority in connection with International Application No. PCT/US2002/012084.
International Preliminary Examination Report issued by the International Bureau in connection with International Application No. PCT/US2002/012084.
Pending claims for U.S. Appl. No. 11/789,361, filed Apr. 23, 2007.
Pending claims for U.S. Appl. No. 11/820,786, filed Jun. 20, 2007.
Pending claims for U.S. Appl. No. 11/894,297, filed Aug. 20, 2007.
Dec. 18, 2003 Office Action issued in connection with U.S. Appl. No. 10/062,308, filed Feb. 1, 2002, now U.S. Patent No. 7,219,016.
Jun. 16, 2004 Office Action issued in connection with U.S. Appl. No. 10/062,308, filed Feb. 1, 2002, now U.S. Patent No. 7,219,016.

(Continued)

*Primary Examiner*—Jerry Lin
(74) *Attorney, Agent, or Firm*—John P. White; Cooper & Dunham LLP

(57) ABSTRACT

Systems and methods for rapidly analyzing cell containing samples, for example to identify morphology or to localize and quantitate biomarkers are disclosed.

8 Claims, 7 Drawing Sheets

OTHER PUBLICATIONS

Apr. 7, 2005 Office Action issued in connection with U.S. Appl. No. 10/062,308, filed Feb. 1, 2002, now U.S. Patent No. 7,219,016.
Oct. 19, 2005 Office Action issued in connection with U.S. Appl. No. 10/062,308, filed Feb. 1, 2002, now U.S. Patent No. 7,219,016.
Apr. 27, 2006 Office Action issued in connection with U.S. Appl. No. 10/062,308, filed Feb. 1, 2002, now U.S. Patent No. 7,219,016.
Nov. 24, 2006 Office Action issued in connection with U.S. Appl. No. 10/062,308, filed Feb. 1, 2002, now U.S. Patent No. 7,219,016.
Mar. 2, 2004 Response to Dec. 18, 2003 Office Action issued in connection with U.S. Appl. No. 10/062,308, filed Feb. 1, 2002, now U.S. Patent No. 7,219,016.
Sep. 16, 2004 Response to Jun. 14, 2004 Office Action issued in connection with U.S. Appl. No. 10/062,308, filed Feb. 1, 2002, now U.S. Patent No. 7,219,016.
Jun. 30, 2005 Response to Apr. 7, 2005 Office Action issued in connection with U.S. Appl. No. 10/062,308, filed Feb. 1, 2002, now U.S. Patent No. 7,219,016.
Feb. 6, 2006 Response to Oct. 19, 2005 Office Action issued in connection with U.S. Appl. No. 10/062,308, filed Feb. 1, 2002, now U.S. Patent No. 7,219,016.
Aug. 28, 2006 Response to Apr. 27, 2006 Office Action issued in connection with U.S. Appl. No. 10/062,308, filed Feb. 1, 2002, now U.S. Patent No. 7,219,016.
Jan. 24, 2007 Response to Nov. 24, 2006 Office Action issued in connection with U.S. Appl. No. 10/062,308, filed Feb. 1, 2002, now U.S. Patent No. 7,219,016.
Jan. 13, 2010 Office Action issued in connection with U.S. Appl. No. 11/789,361, filed Apr. 23, 2007.
Feb. 16, 2010 Response to Jan. 13, 2010 Office Action issued in connection with U.S. Appl. No. 11/789,361, filed Apr. 23, 2007.
May 27, 2010 Office Action issued in connection with U.S. Appl. No. 11/789,361, filed Apr. 23, 2007.
Feb. 3, 2010 Office Action issued in connection with U.S. Appl. No. 11/820,786, filed Jun. 20, 2007.
Mar. 3, 2010 Response to Feb. 3, 2010 Office Action issued in connection with U.S. Appl. No. 11/820,786, filed Jun. 20, 2007.
Feb. 19, 2010 Office Action issued in connection with U.S. Appl. No. 11/894,297, filed Aug. 20, 2007.
Mar. 26, 2010 Response to Feb. 19, 2010 Office Action issued in connection with U.S. Appl. No. 11/894,297, filed Aug. 20, 2007.
Jun. 22, 2010 Office Action issued in connection with U.S. Appl. No. 11/820,786, filed Apr. 23, 2007.
Jun. 22, 2010 Office Action issued in connection with U.S. Appl. No. 11/894,297, filed Aug. 20, 2007.
Supplemental European Search report issued by European Patent Office in connection with International Application No. PCT/US2002/012084.
Agard D A "Optical Sectioning Microscopy: Cellular Architecture in Three Dimensions," *Annual Review of Biophysics and Bioengineering, Annual Reviews Inc.*, vol. 13, Jan. 1, 1984, pp. 191-219.
Official Communication Pursuant to Article 94(3) from European Patent Office dated Oct. 1, 2009 in connection with European Patent Application No. 02739157.2 (national stage of PCT International Application No. PCT/US02/12084).
Feb. 11, 2010 Response to the Official Communication Pursuant to Article 94(3) from European Patent Office issued Oct. 1, 2009 in connection with European Patent Application No. 02739157.2 (national stage of PCT International Application No. PCT/US02/12084).
Examiner's Report issued Nov. 15, 2006 by the Australian Patent Office in connection with Australian Patent Application No. 2002311827, now Australian Patent No. 2002311827 (national stage of PCT International Application No. PCT/US02/12084).
Jul. 15, 2008 Response to the Examiner's Report issued Nov. 15, 2006 by the Australian Patent Office in connection with Australian Patent Application No. 2002311827, now Australian Patent No. 2002311827 (national stage of PCT International Application No. PCT/US02/12084).
Office Action issued Oct. 20, 2009 by the Canadian Patent Office in connection with Canadian Patent Application No. 2442604 (national stage of PCT International Application No. PCT/US02/12084).
Apr. 20, 2010 Response to the Office Action issued Oct. 20, 2009 by the Canadian Patent Office in connection with Canadian Patent Application No. 2442604 (national stage of PCT International Application No. PCT/US02/12084).
English translation of Official Action issued Jul. 4, 2007 by the Japanese Patent Office in connection with Japanese Patent Application No. 2002-583976 (national stage of PCT International Application No. PCT/US02/12084).
English translation of Official Action issued May 19, 2008 by the Japanese Patent Office in connection with Japanese Patent Application No. 2002-583976 (national stage of PCT International Application No. PCT/US02/12084).
English translation of Official Action issued Apr. 10, 2009 by the Japanese Patent Office in connection with Japanese Patent Application No. 2002-583976 (national stage of PCT International Application No. PCT/US02/12084).
Jan. 4, 2008 Response to Japanese Official Action issued issued Jul. 4, 2007 by the Japanese Patent Office in connection with Japanese Patent Application No. 2002-583976 and English translation of the amended claims (national stage of PCT International Application No. PCT/US02/12084).
Oct. 7, 2008 Response to Japanese Official Action issued issued May 19, 2008 by the Japanese Patent Office in connection with Japanese Patent Application No. 2002-583976 and Englisht translation of the amended claims (national stage of PCT International Application No. PCT/US02/12084).
Aug. 17, 2009 Response to Japanese Official Action issued issued Apr. 10, 2009 by the Japanese Patent Office in connection with Japanese Patent Application No. 2002-583976 (national stage of PCT International Application No. PCT/US02/12084).
Santi DV. "The mechanism and structure of thymidylate synthetase," *Nucleic Acids Symp Ser* 1986(17):125-6.
Berger SH, Berger FG. "Thymidylate synthase as a determinant of 5-fluoro-2'-deoxyuridine response in human colonic tumor cell lines," *Mol Pharmacol* 1988;34(4):474-9.
Johnston PG, Drake JC, Trepel J, Allegra CJ. "Immunological quantitation of thymidylate synthase using the monoclonal antibody TS 106 in 5-fluorouracil-sensitive and -resistant human cancer cell lines," *Cancer Res* 1992;52(16):4306-12.
Johnston PG, Lenz HJ, Leichman CG, Danenberg KD, Allegra CJ, Danenberg PV, et al. "Thymidylate synthase gene and protein expression correlate and are associated with response to 5-fluorouracil in human colorectal and gastric tumors," *Cancer Res* 1995;55(7):1407-12.
Leichman CG, Lenz HJ, Leichman L, Danenberg K, Baranda J, Groshen S, et al. "Quantitation of intratumoral thymidylate synthase expression predicts for disseminated colorectal cancer response and resistance to protracted-infusion fluorouracil and weekly leucovorin," *J Clin Oncol* 1997;15(10):3223-9.
Edler D, Glimelius B, Hallstrom M, Jakobsen A, Johnston PG, Magnusson I, et al. "Thymidylate synthase expression in colorectal cancer: a prognostic and predictive marker of benefit from adjuvant fluorouracil-based chemotherapy," *J Clin Oncol* 2002;20(7):1721-8.
Edler D, Kressner U, Ragnhammar P, Johnston PG, Magnusson I, Glimelius B, et al. "Immunohistochemically detected thymidylate synthase in colorectal cancer: an independent prognostic factor of survival," *Clin Cancer Res* 2000;6(2):488-92.
Aschele C, Lonardi S, Monfardini S. "Thymidylate Synthase expression as a predictor of clinical response to fluoropyrimidine-based chemotherapy in advanced colorectal cancer," *Cancer Treat Rev* 2002;28(1):27-47.
Popat S, Matakidou A, Houlston RS. "Thymidylate synthase expression and prognosis in colorectal cancer: a systematic review and meta-analysis," *J Clin Oncol* 2004;22(3):529-36.
Leichman CG. "Thymidylate synthase as a predictor of response," *Oncology* (Williston Park) 1998;12(8 Suppl 6):43-7.
Leichman L, Lenz HJ, Leichman CG, Groshen S, Danenberg K, Baranda J, et al. "Quantitation of intratumoral thymidylate synthase expression predicts for resistance to protracted infusion of 5-fluorouracil and weekly leucovorin in disseminated colorectal cancers: preliminary report from an ongoing trial," *Eur J Cancer* 1995;31A(7-8):1306-10.

Liu J, Schmitz JC, Lin X, Tai N, Yan W, Farrell M, et al. "Thymidylate synthase as a translational regulator of cellular gene expression," *Biochim Biophys Acta* 2002;1587(2-3):174-82.

Camp RL, Chung GG, Rimm DL. "Automated subcellular localization and quantification of protein expression in tissue microarrays," *Nat.Med.* 2002;8(11):1323-1327.

McCabe A, Dolled-Filhart M, Camp RL, Rimm DL. "Automated quantitative analysis (AQUA) of in situ protein expression, antibody concentration, and prognosis," *J Natl Cancer Inst* 2005;97(24):1808-15.

Berger AJ, Kluger HM, Li N, Kielhorn E, Halaban R, Ronai Z, et al. "Subcellular localization of activating transcription factor 2 in melanoma specimens predicts patient survival," 25. *Cancer Res.* 2003;63(23):8103-8107.

Rimm DL, Camp RL, Charette LA, Costa J, Olsen DA, Reiss M. "Tissue microarray: a new technology for amplification of tissue resources," *Cancer J.* 2001;7(1):24-31.

Rimm DL, Camp RL, Charette LA, Olsen DA, Provost E. "Amplification of tissue by construction of tissue microarrays," *Exp Mol Pathol* 2001;70(3):255-64.

Giltnane JM, Rimm DL. "Technology insight: Identification of biomarkers with tissue microarray technology," *Nat Clin Pract Oncol* 2004;1(2):104-11.

Camp RL, Dolled-Filhart M, Rimm DL. "X-tile: a new bio-informatics tool for biomarker assessment and outcome-based cut-point optimization," 9. *Clin.Cancer Res.* 2004;10(21):7252-7259.

Raeside DE. "Monte Carlo principles and applications," *Phys Med Biol* 1976;21(2):181-97.

Camp RL, Charette LA, Rimm DL. "Validation of tissue microarray technology in breast carcinoma," 50. *Lab Invest* 2000;80(12):1943-1949.

Kucera R, Paulus H. "Localization of the deoxyribonucleotide biosynthetic enzymes ribonucleotide reductase and thymidylate synthase in mouse L cells," *Exp Cell Res* 1986;167(2):417-28.

Johnston PG, Liang CM, Henry S, Chabner BA, Allegra CJ. "Production and characterization of monoclonal antibodies that localize human thymidylate synthase in the cytoplasm of human cells and tissue," *Cancer Res* 1991;51(24):6668-76.

Bissoon-Haqqani S, Moyana T, Jonker D, Maroun JA, Birnboim HC. "Nuclear expression of thymidylate synthase in colorectal cancer cell lines and clinical samples," *J Histochem Cytochem* 2006;54(1):19-29.

Wong NA, Brett L, Stewart M, Leitch A, Longley DB, Dunlop MG, et al. "Nuclear thymidylate synthase expression, p53 expression and 5FU response in colorectal carcinoma," *Br J Cancer* 2001;85(12):1937-43.

International Preliminary Report on Patentability issued by the International Bureau in connection with International Application No. PCT/US2007/016014.

Written Opinion of the International Searching Authority issued by the International Searching Authority (ISA/US) in connection with International Application No. PCT/US2007/016014.

International Search Report issued by the International Bureau in connection with International Application No. PCT/US2007/016014.

Cascinue S. et al., "Thymidylate synthase protein expression in advanced colon cancer: correlation with the site of metastasis and the clinical response to Leucovorin-modulated bolus 5-fluorouracil," *Clinical Cancer Research*, Aug. 1999, vol. 5, pp. 1996-1999.

Santini D. et al. "Thymidylate synthase expression in normal colonic mucosa: a predictive marker of toxicity in colorectal cancer patients receiving 5-fluorouracil-based adjuvant chemotherapy," *Oncology*, 2004, vol. 67, pp. 135-142.

Apr. 8, 2009 Response to the Official Communication Pursuant to Rules 161 and 162 issued by the European Patent Office in connection with European Patent Application No. 07810453.6 (national stage of PCT International Application No. PCT/US07/016014).

International Preliminary Report on Patentability issued by the International Bureau in connection with International Application No. PCT/US2008/08229.

International Preliminary Report on Patentability issued by the International Bureau in connection with International Application No. PCT/US2008/08007.

Pending claims for U.S. Appl. No. 12/215,458, filed Jun. 27, 2008.

"Tamoxifen for early breast cancer: an overview of the randomised trials," Early Breast Cancer Trialists' Collaborative Group, Lancet, 351:1451-67, 1998.

Dowsett M, Houghton J, Iden C, et al. "Benefit from adjuvant tamoxifen therapy in primary breast cancer patients according oestrogen receptor, progesterone receptor, EGF receptor and HER2 status," Ann Oncol 17:818-26, 2006.

Arpino G, Green SJ, Allred DC, et al. "HER-2 amplification, HER-1 expression, and tamoxifen response in estrogen receptor-positive metastatic breast cancer: a southwest oncology group study." Clin Cancer Res 10:5670-6, 2004.

Arpino G, Weiss H, Lee AV, et al. "Estrogen receptor-positive, progesterone receptor-negative breast cancer: association with growth factor receptor expression and tamoxifen resistance," J Natl Cancer Inst 97:1254-61, 2005.

Linke SP, Bremer TM, Herold CD, et al. "A multimarker model to predict outcome in tamoxifen-treated breast cancer patients," Clin Cancer Res 12:1175-83, 2006.

Osborne CK, Shou J, Massarweh S, et al. "Crosstalk between estrogen receptor and growth factor receptor pathways as a cause for endocrine therapy resistance in breast cancer," Clin Cancer Res 11:865s-70s, 2005.

Osborne CK. "Tamoxifen in the treatment of breast cancer," N Engl J Med 339:1609-18, 1998.

Johnston SR. "Clinical efforts to combine endocrine agents with targeted therapies against epidermal growth factor receptor/human epidermal growth factor receptor 2 and mammalian target of rapamycin in breast cancer," Clin Cancer Res 12:1061s-1068s, 2006.

Schlessinger J. "Cell signaling by receptor tyrosine kinases," Cell 103:211-25, 2000.

Nicholson RI, McClelland RA, Gee JM, et al. "Epidermal growth factor receptor expression in breast cancer: association with response to endocrine therapy," Breast Cancer Res Treat 29:117-25, 1994.

Nicholson RI, McClelland RA, Finlay P, et al. "Relationship between EGF-R, c-erbB-2 protein expression and Ki67 immunostaining in breast cancer and hormone sensitivity," Eur J Cancer 29A:1018-23, 1993.

Gee JM, Robertson JF, Gutteridge E, et al. "Epidermal growth factor receptor/HER2/insulin-like growth factor receptor signalling and oestrogen receptor activity in clinical breast cancer," *Endocr Relat Cancer* 12 Suppl 1:S99-S111, 2005.

Camp RL, Chung GG, Rimm DL. "Automated subcellular localization and quantification of protein expression in tissue microarrays," *Nat Med* 8:1323-7, 2002.

McCabe A, Dolled-Filhart M, Camp RL, et al. "Automated quantitative analysis (AQUA) of in situ protein expression, antibody concentration, and prognosis," *J Natl Cancer Inst* 97:1808-15, 2005.

Ryden L, Jonsson PE, Chebil G, et al. "Two years of adjuvant tamoxifen in premenopausal patients with breast cancer: a randomised, controlled trial with long-term follow-up," *Eur J Cancer* 41:256-64, 2005.

Ryden L, Jirstrom K, Bendahl P-O, et al. "Tumor-specific expression of vascular endothelial growth factor receptor 2 but not vascular endothelial growth factor or human epidermal growth factor receptor 2 is associated with impaired response to adjuvant tamoxifen in premenopausal breast cancer," *J Clin Oncol* 23:4695-4704, 2005.

Christensen TA, Reiter JL, Baron AT, et al. "Generation and characterization of polyclonal antibodies specific for human p110 sEGFR," *Hybrid Hybridomics* 21:183-9, 2002.

Dolled-Filhart M, McCabe A, Giltnane J, et al. "Quantitative in situ analysis of beta-catenin expression in breast cancer shows decreased expression is associated with poor outcome," *Cancer Res* 66:5487-94, 2006.

Rubin MA, Zerkowski MP, Camp. RL, et al. "Quantitative determination of expression of the prostate cancer protein alpha-methylacyl-CoA racemase using automated quantitative analysis (AQUA): a novel paradigm for automated and continuous biomarker measurements," *Am J Pathol* 164:831-40, 2004.

Jonat W, Pritchard KI, Sainsbury R, et al. "Trends in endocrine therapy and chemotherapy for early breast cancer: a focus on the premenopausal patient," *J Cancer Res Clin Oncol* 132:275-86, 2006.

Reiter JL, Maihle NJ. "Characterization and expression of novel 60-kDa and 110-kDa EGFR isoforms in human placenta," *Ann N Y Acad Sci* 995:39-47, 2003.

Schiff R, Massarweh SA, Shou J, et al. "Advanced concepts in estrogen receptor biology and breast cancer endocrine resistance: implicated role of growth factor signaling and estrogen receptor coregulators," *Cancer Chemother Pharmacol* 56 Suppl 1:10-20, 2005.

Ciardiello F, Tortora G. "Epidermal growth factor receptor (EGFR) as a target in cancer therapy: understanding the role of receptor expression and other molecular determinants that could influence the response to anti-EGFR drugs," *Eur J Cancer* 39:1348-54, 2003.

Camp RL, Dolled-Filhart M, King BL, et al. "Quantitative Analysis of Breast Cancer Tissue Microarrays Shows That Both High and Normal Levels of HER2 Expression Are Associated with Poor Outcome," *Cancer Res* 63:1445-8, 2003.

Howell A, Cuzick J, Baum M, et al. "Results of the ATAC (Arimidex, Tamoxifen, Alone or in Combination) trial after completion of 5 years' adjuvant treatment for breast cancer," *Lancet* 365:60-2, 2005.

Punglia RS, Kuntz KM, Winer Ep, et al. "The impact of tumor progesterone receptor status on optimal adjuvant endocrine therapy for postmenopausal patients with early-stage breast cancer: a decision analysis," *Cancer* 106:2576-82, 2006.

International Search Report issued by the International Bureau in connection with International Application No. PCT/US2008/08229.

Written Opinion of the International Searching Authority issued by the International Searching Authority (ISA/US) in connection with International Application No. PCT/US2008/08229.

Matsumoto et al. "Markers of cell proliferation and expression of melanosomal antigen in lymphangioleimyomatosis," *Am. J. Respir. Cell. Mol. Biol.* Sep. 1999 (19.1999), vol. 21, No. 3 pp. 372-326.

Vollmer et al. "Use of Bayes Rule and MIB-1 Proliferation Index to Discriminate Spitz Nevus From Malignant Melanoma," *Am. J. Clin. Pathol.* 2004, vol. 122, pp. 499-505.

Sundram et al. "Expression of the B-Cell Proliferation Marker MUM1 by Melanocytic Lesions and Comparison with S100, gp100 (HMB45), and MelanA," *Mod. Pathol.* 3003, vol. 16, No. 8 pp. 802-810.

International Search Report issued by the International Bureau in connection with International Application No. PCT/US2008/08007.

Written Opinion of the International Searching Authority issued by the International Searching Authority (ISA/US) in connection with International Application No. PCT/US2008/08007.

Konenen, et al. "Tissue Microarrays for High-Throughput Molecular Profiling of Tumor Specimens," *Nature Medicine*, Jul. 1998, vol. 4, No. 7, pp. 844-847.

Bubendor et al. "Survey of Gene Amplifications during Prostate Cancer Progression by High-Throughput Fluorescence in Situ Hybridication on Tissue Microarrays," *Cancer Research* (1999) vol. 59, pp. 803-806.

Sep. 22, 2010 Response to Jun. 22, 2010 Office Action issued in connection with U.S. Appl. No. 11/894,297.

Sep. 22, 2010 Response to Jun. 22, 2010 Office Action issued in connection with U.S. Appl. No. 11/820,786.

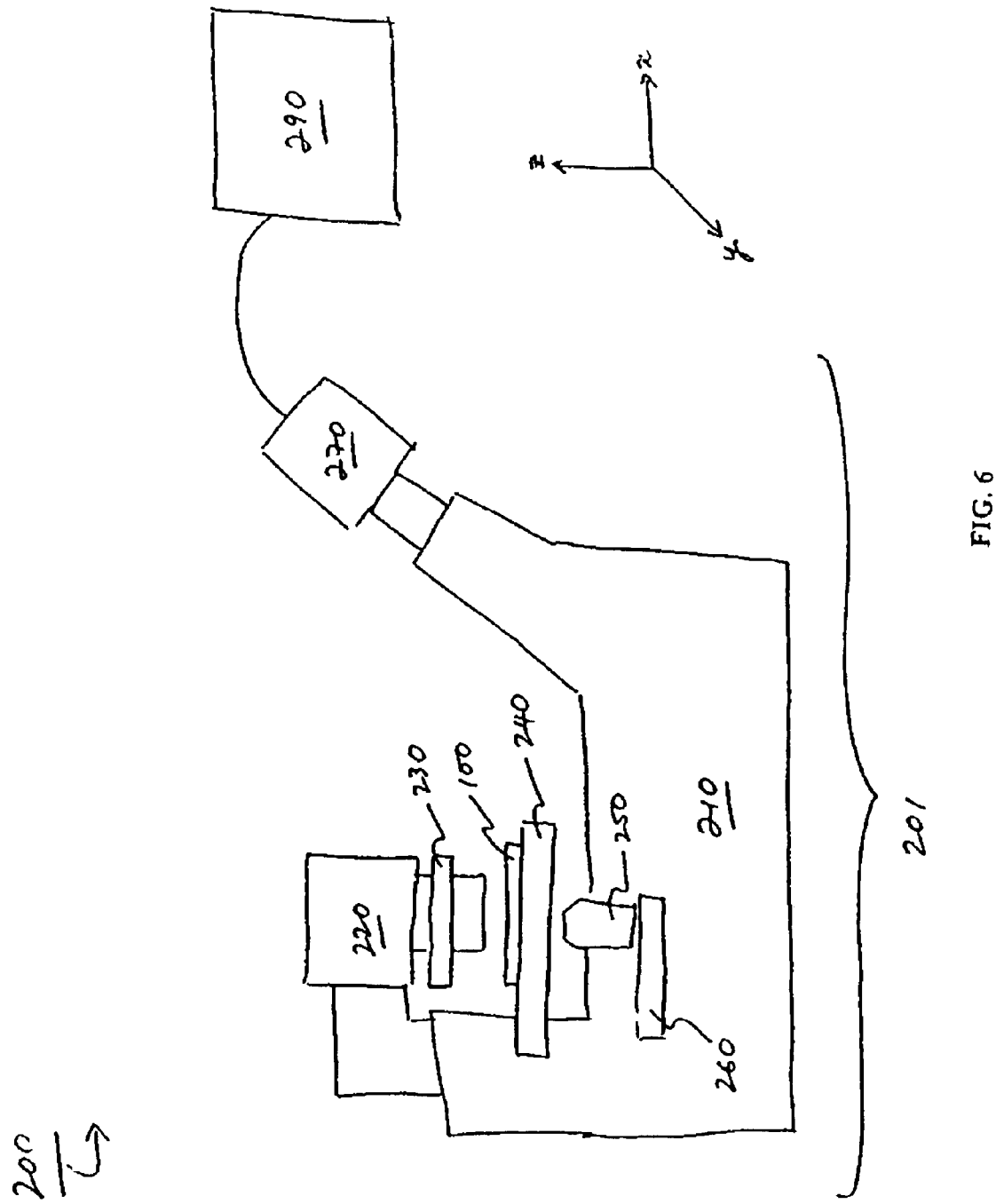

SYSTEMS AND METHODS FOR AUTOMATED ANALYSIS OF CELLS AND TISSUES

This application is a divisional of U.S. Ser. No. 11,789,361, filed Apr. 23, 2007, which is a continuation of U.S. Ser. No. 10/062,308, filed Feb. 1, 2002, now U.S. Pat. No. 7,219,016, issued May 15, 2007, and claims the benefit of U.S. Provisional Application Nos. 60/334,723, filed Oct. 31, 2001 and 60/285,155, filed Apr. 20, 2001, the content of each of which is hereby incorporated herein by reference into the application.

This invention was made with support under United States Government Grant No. 5K08ES011571 from the National Institute of Health. Accordingly, the United States Government has certain rights in the subject invention.

1. BACKGROUND OF THE INVENTION

Tissue microarray technology offers the opportunity for high throughput analysis of tissue samples (Konen, J. et al., *Nat. Med.* 4:844-7 (1998); Kallioniemi, O. P. et al., *Hum. Mol. Genet.* 10:657-62 (2001); Rimm, D. L. et al., *Cancer J.* 7:2431 (2001)). For example, the ability to rapidly perform large scale studies using tissue microarrays can provide critical information for identifying and validating drug targets/prognostic markers (e.g. estrogen receptor (ER) and HER2/neu) and candidate therapeutics.

Automated quantitative analysis of tissue samples in microarrays, however, presents several challenges, including heterogeneity of tissue sections, subcellular localization of staining, and the presence of background signals. For example, depending on the type of tumor or tissue section being analyzed, the area of interest may represent nearly the entire sample, or only a small percentage. For instance, a pancreatic carcinoma or lobular carcinoma of the breast with substantial desmoplastic response may show stromal tissue representing a large percentage of the total area. If the goal of the assay is to determine epithelial cell expression of a given marker, a protocol must be used that evaluates only that region. The protocol must not only be able to select the region of interest but also normalize it, so that the expression level read from any given area can be compared with that of other areas. Subcellular localization presents similar challenges. Comparisons of nuclear or membranous staining, for example, are quite different from those in total cytoplasmic staining.

Certain methods (including confocal and convolution/deconvolution microscopy) have been used to quantify expression of proteins at the cellular (or sub-cellular) level within a single high power field (Robinson, J. P. *Methods Cell. Biol.* 63:89-106 (2001); Shaw, P. *Histochem. J.* 26:687-9)$_4$ (1994)). However, these are computationally intensive and laborious techniques, which operate on multiple serial images. As a result, the current standard for analysis of tissue microarrays, like tissue sections, is conventional pathologist-based analysis and grading of the sample according to scale.

Most biomarkers exhibit a parametric (normal, "bell-shaped") distribution, and consequently are best analyzed by a continuous scale (e.g., 0 to 1000). Unfortunately, manual observation tends to be nominal (e.g. 1+, 2+, 3+), primarily because the human eye in unable to reliably distinguish subtle differences in staining intensity. Several methods have been developed to translate nominal manual observations into a continuous scale. Foremost among these is the H-score where the percent of positively stained cells (0 to 100) is multiplied by the staining intensity (e.g. 0 to 3) to make a theoretically continuous scale (0 to 300). However, the inability to detect subtle differences in staining intensity, particularly at the low and high ends of the scale, as well as the tendency to round scores (e.g. 50% at 3+ for a score of 150, versus 47% at 3+ for a score of 141), limits the effectiveness of the H-score.

Automated systems and methods for rapidly analyzing tissue, including tissue microarrays, that permit the identification and localization of identified biomarkers within tissues and other cell containing samples, are needed.

2. SUMMARY OF THE INVENTION

In one aspect, the invention features systems and methods for rapidly analyzing cell containing samples to localize and quantitate particular biomarkers within cells. In one embodiment, the method is implemented by a computer and superimposes an image of the biomarker against an image of a user defined area within the cell to determine whether the biomarker is within the user defined area.

In another aspect, the invention features an algorithm that facilitates the optical analysis of an array of biological samples, despite image irregularities, distortions, varying topologies, and the absence of one or more elements.

Analysis of patient samples according to the systems and processes described herein can be useful diagnostically (e.g. to identify patients who have a particular disease, have been exposed to a particular toxin or are responding well to a particular therapeutic or organ transplant) and prognostically (e.g. to identify patients who are likely to develop a particular disease, respond well to a particular therapeutic or be accepting of a particular organ transplant). As new and better markers of disease become identified in the post-genomic era, the instant described processes, which not only quantitate the markers, but also determine their relative location within a cell, will increase in applicability.

Automated analysis of cell containing preparations, as described herein, can provide a rapid assessment of the prognostic benefit of biomarkers. In addition, these automated techniques can identify associations that are typically not revealed using manual techniques. Also, automated analysis can better discern subtle differences in staining intensity, particularly at the upper and lower extremes. The ability to detect low level expression and distinguish it from no expression can provide important prognostic information. Furthermore, analysis of the sub-cellular distribution of certain biomarkers may elucidate previously unrecognized associations with patient survival.

Other features, objects, and advantages of the invention will be apparent from the following figures, detailed description and claims.

3. DESCRIPTION OF THE FIGURES

FIG. 6 shows an optical microscope station.

4. DETAILED DESCRIPTION

4.1 General

In general, described herein are a collection of techniques that can be used for rapid, automated analysis of cell containing samples, including tissues and tissue microarrays. While these techniques build on one another and are described as a cohesive process, each technique has wide applicability and may be used individually or in combinations other than those described below.

In one embodiment is featured a technique to identify the location of spots within an image. The technique, termed "spotfinder", can flexibly identify such locations despite image irregularities, distortions, varying topologies, and the absence of one or more elements. Although the process is described for locating the position of histospots and identifying missing histospots within tissue microarray images, the technique has broader application. More specifically it can be used to locate elements and identify missing elements in any collection of elements. Moreover, the process can be used on arrays of virtually any dimension and comprising a variety of elements. The specimens are not limited by size or shape, nor must they be regularly spaced.

In another embodiment is featured a technique that can be used alone or in conjunction with spotfinder to optically localize and quantitate a biomarker within a cell. Though an image of a cellular preparation typically features two dimensions, cellular preparations feature depth. For example, one cellular feature may rest atop another. This overlap can potentially confuse image analysis software. A technique described herein, dubbed RESA (Rapid Exponential Subtraction Algorithm), can approximate a three dimensional image by subtracting out-of-focus image elements. Thus, the impact of background features on an image can be reduced, permitting better image analysis.

Another technique described herein, dubbed PLACE (Pixel Based Locale Assignment Compartmentalization of Expression), distinguishes between different cellular characteristics. For example, the technique can determine the location of subcellular compartments within individual cells. A computer implementing this technique can, for instance, measure the relative intensities of images derived from compartment-specific stains on a pixel-by-pixel basis. The computer then determines for individual pixels within an image, the likelihood that the pixel corresponds to a particular locale or user defined area within the cell. Such analysis permits the computer to assign signals to a sub-cellular compartment with an established degree of accuracy (e.g., 95%). The technique can co-localize signals associated with particular biomarkers with images of defined locales within cells.

Figure 1:
FIGS. 1(A-D) shows separate monochromatic images of a colon carcinoma taken after staining with fluorescently-tagged markers and combined into a single color image as follows: DAPI (to visualize nuclei, blue), anti-cytokeratin (to distinguish tumor from non-tumor elements, green), and anti-alpha-catenin (to visualize cell membranes, red).
Figure 1:
Figure 1:
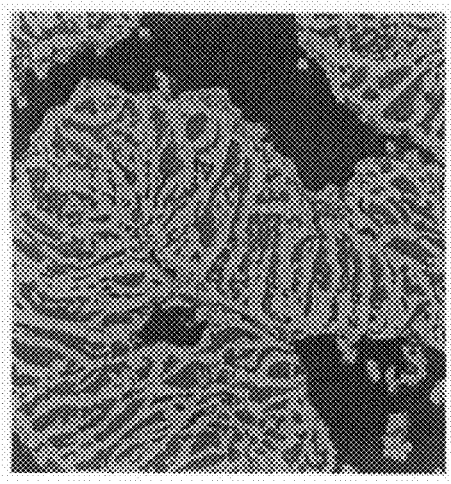
Figure 1:
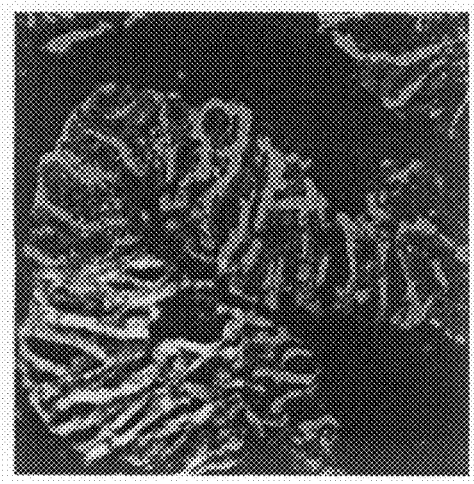
Figure 2:
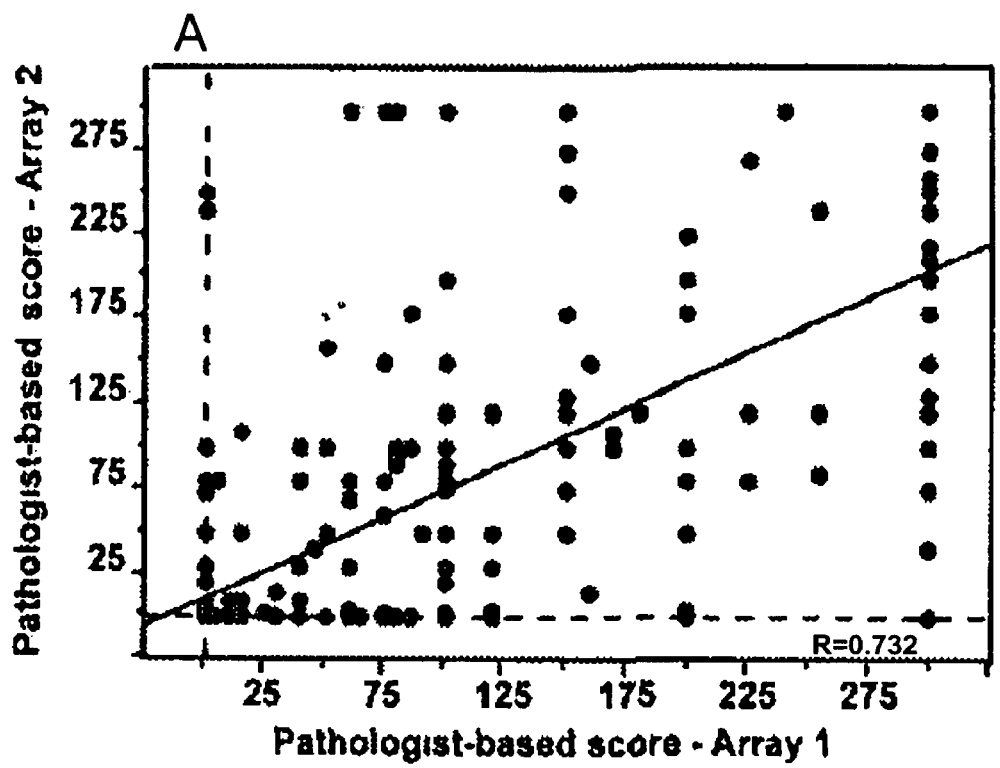
FIG. 2(A-D) shows a regression comparison of automated and pathologist-based scoring of estrogen receptor levels.
Figure 2:
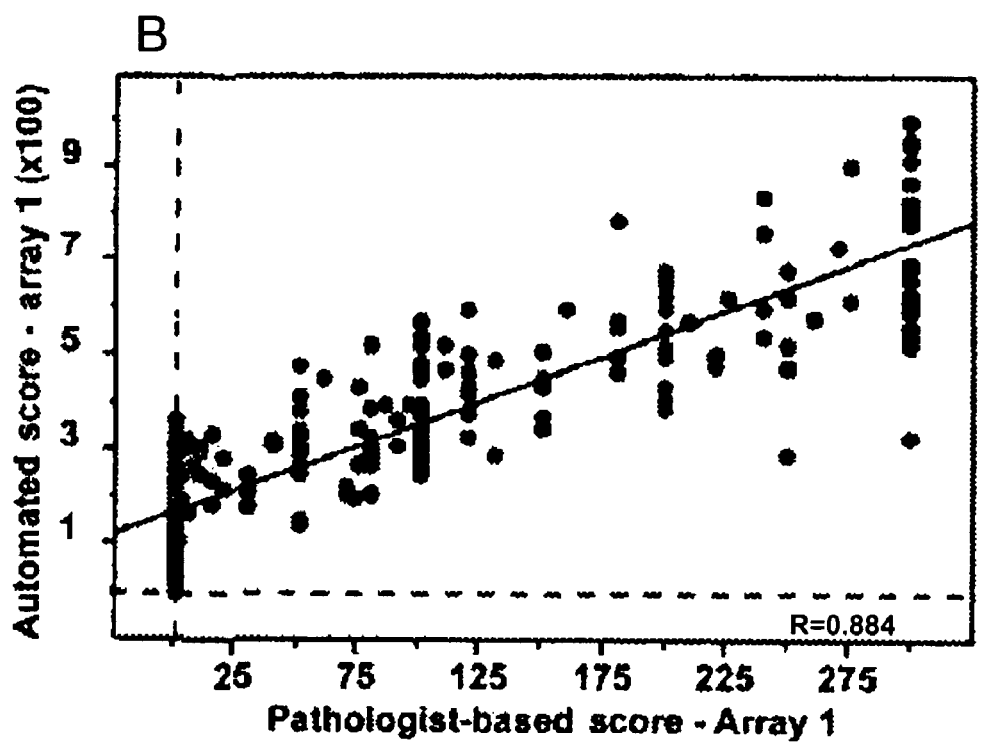
Figure 2:
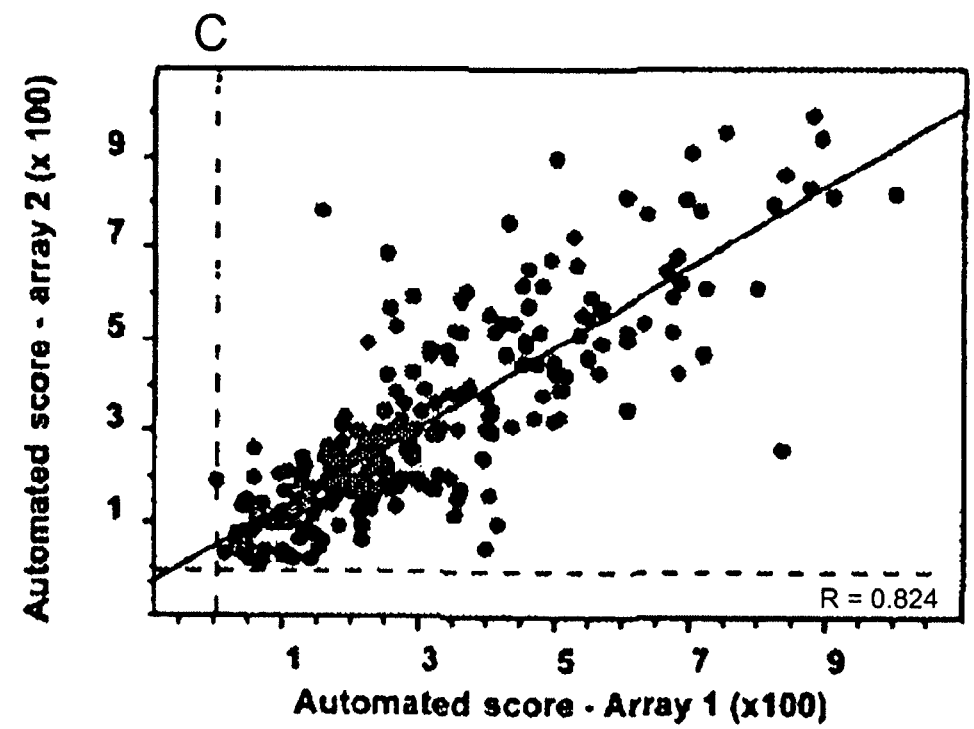
Figure 2:
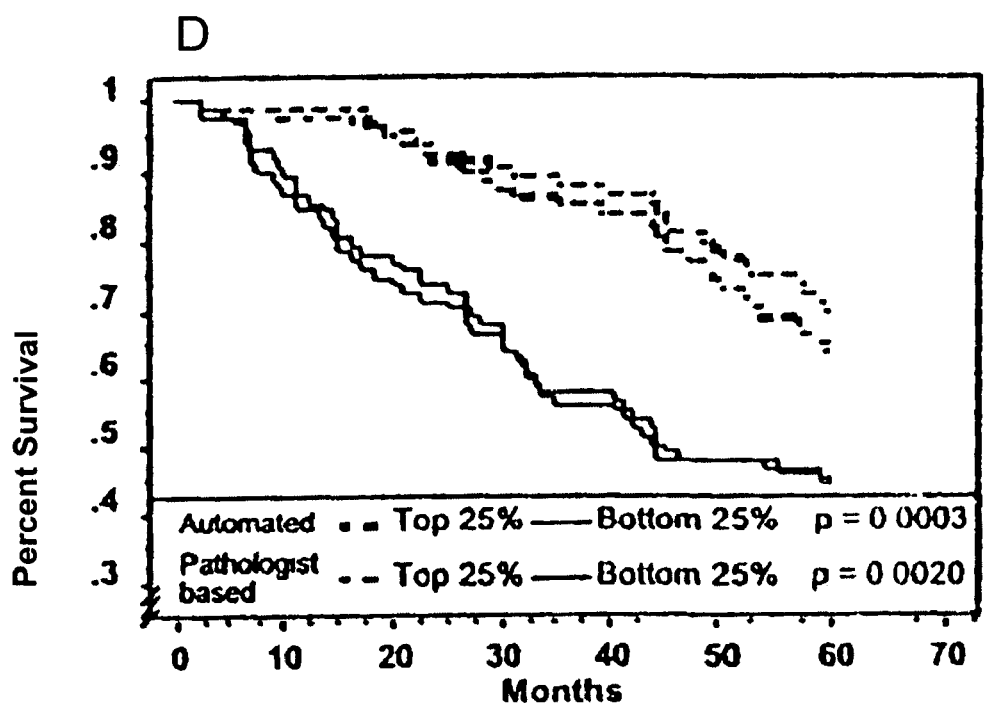

Use of these techniques can enhance both the speed and accuracy of automated microarray analysis. FIG. 1 shows separate monochromatic images of a colon carcinoma taken after staining with fluorescently-tagged markers and combined into a single color image as follows: DAPI (to visualize nuclei, blue), anti-cytokeratin (to distinguish tumor from non-tumor elements, green), and anti-alpha-catenin (to visualize cell membranes, red) (panel A). Note the significant degree of overlap between the subcellular compartments. A monochromatic image of the biomarker β-catenin, is taken (panel B, inset) and the intensity of each pixel in the image redistributed according to the relative signal intensity of the various compartments in panel A (blue=nuclei, red=membrane, green=cytoplasm).

Although the β-catenin expression in this tumor is predominantly membrane-associated, the significant overlap in compartments in panel A incorrectly assigns a significant amount of the signal to the nucleus (magenta and blue pixels, panel B). To aid in the removal of overlapping signals, the monochromatic image of each sub-cellular compartment is exponentially subtracted from an out-of-focus image. Panel C shows a composite of the exponentially subtracted images of DAPI and anti-alpha-catenin (blue and red, respectively), shown on a mask derived from the anti-cytokeratin mask (green pixels). Pixels with too much overlap between channels are negated (<5%), as are non-tumor areas, as defined by a mask generated from the anti-cytokeratin image. In panel D, the signal intensity from an exponentially subtracted image of the biomarker (β-catenin, inset) is then redistributed according to the compartments defined in panel C. This results in more accurate assignment of the biomarker to the membrane compartment, which can have important prognostic significance. Since membrane-associated beta-catenin stabilizes cadherin-mediated adhesion by facilitating the cytoskeletal attachment of adhesion complexes, while nuclear-associated beta-catenin acts as a transcription factor, which up-regulates several genes important in cell proliferation and invasion and is considered an oncogene in this capacity, expression of beta-catenin alone does not provide prognostic information. However its localization in the nucleus can be an important indicator of carcinogenesis.

1. Spot-Finder

Figure 3:
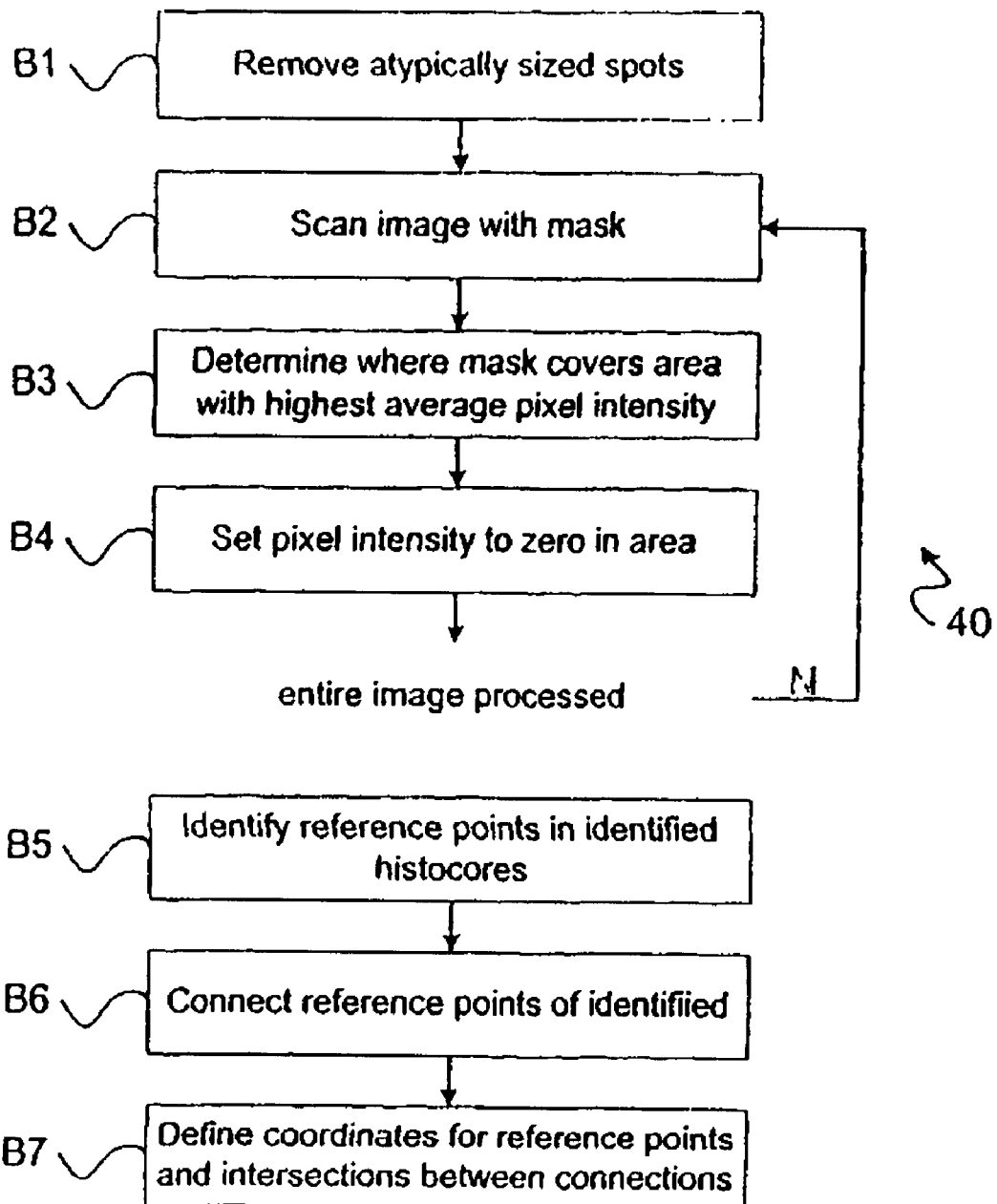
FIG. 3 is a flowchart of a method for identifying and accounting for the relative location of spots within an array.

In one embodiment, shown in FIG. 3, the computer removes B1 any atypically sized spots from the image. Atypically sized spots may include, for example, images of fused spots and/or debris. The computer performs the process automatically, though in other embodiments it may allow use of user input to facilitate the process.

The computer then creates or accesses an opaque virtual mask that is the size and shape of a typical spot. Using the virtual mask, the computer scans B2 the image to determine B3 where the mask first covers an area with the highest average pixel intensity. The computer monitors the total intensity of the image during the scan and, because the mask is opaque, identifies the position of the mask when the total image intensity is minimized. The computer identifies this area as the first spot and sets B4 the pixels within this area to have zero intensity. The computer also sets additional pixels within a predefined area around this area to have zero intensity. This helps to differentiate between overlapping spots.

After identifying the first spot, the computer again scans B2 the image using the mask to find the next area with the highest average pixel intensity. When the next area is found, the computer identifies it as the second spot and sets the pixels in and surrounding this area to have zero intensity. The computer repeats this process until it can no longer find areas of the image with sufficient intensity to qualify as spots.

The computer then identifies B5 a reference point (e.g., the center) in each spot, and draws a line connecting the reference point of each spot to each nearest neighboring spot reference point, above, below, to the left, and to the right. If the computer cannot identify a nearest neighbor in any of these directions (i.e., the spot is on the edge of the array), the computer draws a line from the center of the spot to the nearest edge of the image.

2. RESA and PLACE

Once the location of an image area of interest is determined, an optical microscope can obtain a high resolution image at an appropriate wavelength to identify cellular features of interest. These features include the biomarker, also referred to as the "signal", the cells of interest within the tissue section (referred to as the "cell mask"), or a user defined location within the cell mask, also referred to as the "locale". The signal, the cell mask, and the locale are referred to as "channels".

Figure 4:
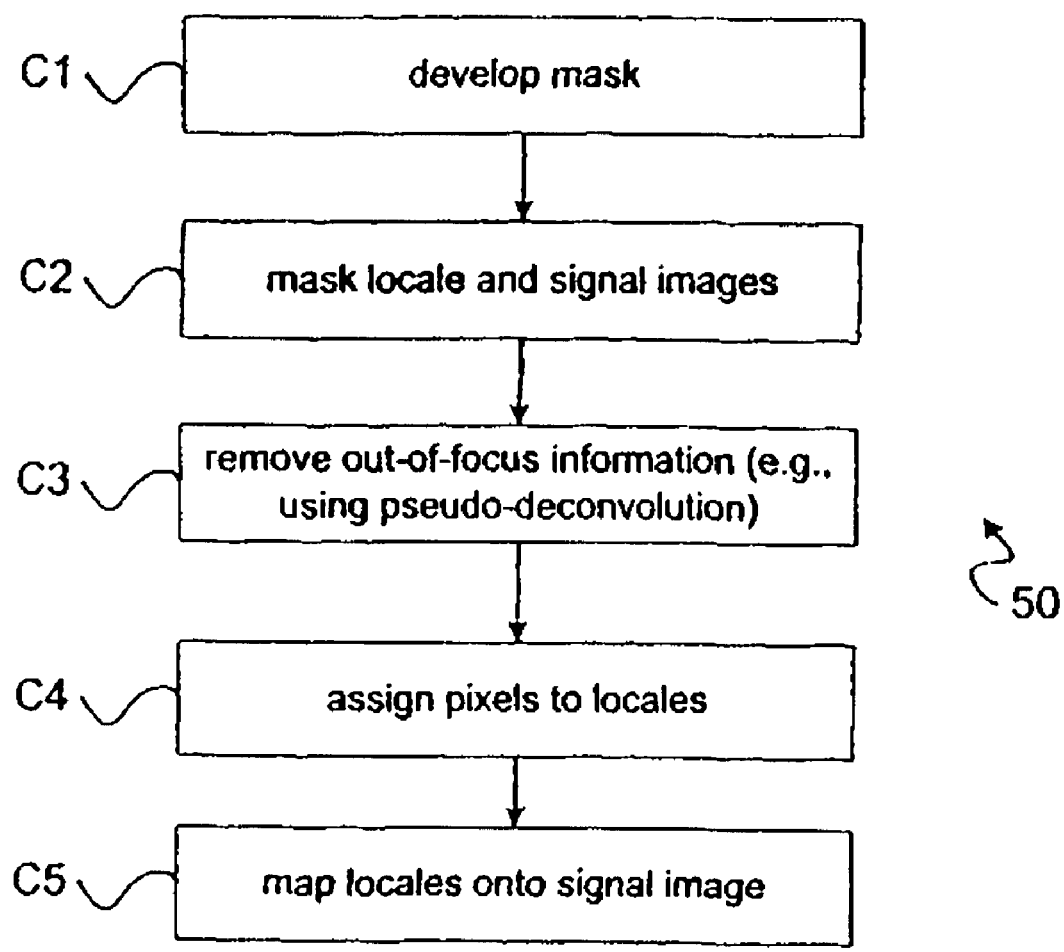
FIG. 4 is a flowchart of a process for localizing a signal (e.g. a biomarker) within a locale.

Referring to FIG. 4, a process 50 determines the region of interest in the images by developing a mask from the cell mask channel (step C1). Next, the process applies this mask to the locale and signal channels (step C2). The process then removes out-of-focus information from the masked images, for example, in a process of pseudo-deconvolution (step C3). Next, in a "pixel assignment" phase, the process identifies subcellular features in the image, assigning pixels in the image to the locales (step C4). Once the pixels are assigned, the computer maps the locales onto the signal image (step C5), and quantifies the amount of biomarker in each locale. This phase is referred to as "signal assignment". These steps are described in greater detail below.

Masking

During this process, the software identifies a region of interest in the image of the stained cells of interest (i.e., the cell mask channel). The software masks the locale and signal channels avoiding unnecessary analyses of areas outside the region of interest.

To identify a region of interest, the computer determines a threshold intensity for the cell mask channel. Once determined, the computer redistributes the pixel intensities in a binary redistribution. In other words, the computer sets the intensity of each pixel below the threshold to zero, and sets the remaining pixels to have the maximum intensity (e.g., for an 8-bit image the maximum intensity is 255). The set of pixel locations set to maximum intensity are referred to as the mask. Subsequent procedures on the other images in the image stack are performed on the pixel locations corresponding to the mask.

The threshold intensity is related to the intensity of the background in the image, which the computer determines by first binning each pixel according to its intensity (e.g., in an 8-bit image each pixel will have an intensity from 0 to 255). In some embodiments, the background corresponds to the largest bin (i.e., the most common pixel intensity). In other embodiments, the background corresponds to the second largest bin. This occurs in some cases when the tissues autofluoresce and the largest bin corresponds to an area of fluorescing tissue instead of the fluorescing histochemical stains. In either case, the computer assumes that the background intensity is lower than a certain fraction of the maximum intensity (e.g., less than half the maximum intensity).

Bin size is plotted versus intensity to yield a histogram. The maximum peak in the histogram corresponds to the largest bin. In embodiments where the largest bin corresponds to the background, the computer assigns the maximum peak intensity as the background intensity. In other embodiments, where the background corresponds to the second largest bin, the histogram has a second peak at a lower intensity than the maximum peak. So, if the second peak is at least a certain fraction of the size of the maximum peak (e.g., at least five percent), then the computer assigns the second peak intensity as the background intensity of the image.

Once established, the computer adds an additional factor to the background intensity to determine the threshold intensity. For an 8-bit image, this factor equals $D(\frac{1}{5})/10$ multiplied by a user defined input (usually 0.5). Here, $D(\frac{1}{5})$ is the quintile distribution of the binned pixels, which is determined as $$D(\tfrac{1}{5}) = \langle I \rangle_{top\ 20} - \langle I \rangle_{bottom\ 20},$$

where $\langle I \rangle_{top\ 20}$ is the mean pixel intensity of the pixels within the top $20^{th}$ percentile, and $\langle I \rangle_{bottom\ 20}$ is the mean pixel intensity of pixels in the bottom $20^{th}$ percentile.

Pixels with intensity at or above the threshold intensity are assigned to the mask.

The mask is then further modified according to user-defined parameters and image processing techniques. For example, the mask can be dilated or eroded so that the mask area matches a user-defined value, or have holes of a particular (user-defined) size within it filled. The user-defined parameters for creating the mask may be adjusted after analyzing a small number of sample histospot images, prior to running the entire array.

After developing the mask, the computer applies the mask to the images in the image stack, identifying the region of interest in each of these images as the pixel locations corresponding to the mask pixel locations.

Background Reduction

As shown, the process 50 reduces C3 the impact of the out-of-focus information from the image. For example, the process 50 may use a pseudo deconvolution technique. While the pixels of the remaining image are reduced in intensity, the image information represents a thinner virtual slice through the top of the tissue. Furthermore, pseudo-deconvolution enhances the interfacial areas between the higher stain intensity and lower stain intensity areas of the image by increasing the contrast between these areas.

The computer performs pseudo-deconvolution on the locale (cellular compartments) and signal (i.e., cellular components) channels. The computer first masks the images of these channels, reducing the number of pixels to be analyzed. The computer analyzes two images of each channel. The first image is an in-focus image (i.e., an image of the top of the histospot). The second image is a slightly out-of-focus image, produced by placing the focal plane slightly below the bottom of the tissue (e.g., for a five micron thick histospot, the focal plane of this image is located about eight microns below the top of the histospot).

For each pixel location, the computer subtracts a percentage of the out-of-focus image pixel intensity, $I_{out-of-focus}$, from the corresponding in-focus image pixel intensity, $I_{in-focus}$. The computer determines the adjusted pixel intensity, $I_{new\ pixel}$, using the quartile distribution, $D(\frac{1}{4})$, of the in-focus image as follows:

$$I_{new\ pixel} = I_{in-focus} - I_{out-of-focus} \times \left(\frac{I_{max} - I_{in-focus}}{I_{max}}\right)^{\psi},$$

where $I_{max}$ is the maximum pixel intensity (e.g., 255 for an 8-bit image), and $\psi$ is calculated from $$\psi = \alpha \times D(\tfrac{1}{4})^{-\beta},$$

which was developed from an empiric assessment of a library of images Optical deconvolutions were judged visually and the $\psi$ for each was plotted versus the quartile distribution for the in-focus image. Regression analysis of the empiric data yielded values for the fitting-parameters (i.e., $\alpha$ is about 80 and $\beta$ is about 1.19). The quartile distribution is determined from $$D(\tfrac{1}{4}) = \langle I \rangle_{top\ 25} - \langle I \rangle_{bottom\ 25},$$

where $\langle I \rangle_{top\ 25}$ is the mean pixel intensity of the pixels within the top $25^{th}$ percentile, and $\langle I \rangle_{bottom\ 25}$ is the mean pixel intensity of pixels in the bottom 25$^{th}$ percentile. Conceptually, low intensity pixels in images with a low D(¼) (i.e. a low signal to noise ratio) are subtracted less heavily than low intensity pixels from images with a high D(¼).

The value of ψ may be refined by determining the percent of signal intensity remaining after pseudo-deconvolution within the masked area and comparing it to a predefined value for that channel. If the percent is, for example, greater than the predefined value then the pseudo-deconvolution stops. Otherwise, the computer iteratively increases the value of ψ until the predefined percent of signal intensity is reached. The predefined value is the expected percentage of the mask covered by a channel.

After pseudo-deconvolution, each pixel of the resulting images is assigned to a locale in a process referred to as pixel assignment.

Pixel Based Locale Assignment Compartmentalization of Expression (PLACE)

During the pixel assignment phase, the computer assigns an identity based on the relative intensity of that pixel location in each of the locale channel images (i.e., the images of the stained locales). For example, during this phase the computer decides for each pixel location in the image whether it belongs to the nucleus, the membrane, or the cytoplasm. The computer does not make an assignment to pixels that it cannot assign within a user-defined degree of confidence (e.g., 95%). Higher levels of confidence eliminate more pixels from the analysis.

In general, for each pixel location in two locale images the computer reads a pixel intensity and compares each intensity value to a predetermined threshold intensity value. If the intensity value of only one locale is greater than the threshold, the computer assigns the pixel location to that locale. If both the intensity values are greater than their respective thresholds, the computer compares the intensity values from each locale, and assigns the identity of the locale having the greater intensity to that pixel location. If both the pixel intensities are below their threshold values, the computer assigns the pixel to a third locale.

After repeating the above for pixel locations in the images, the computer calculates the area of each locale, and compares the result to a predetermined (expected) coverage fraction. If the calculated coverage fraction (e.g., number of nuclear locale pixels/number of masked pixels) is greater than the predetermined coverage fraction, then the computer removes the pixels having the lowest intensity from the locale. The computer continues to remove the lowest intensity pixels until the coverage fraction is reduced to about the predetermined coverage fraction.

The following is an example of how this process works. The membrane locale and the nucleus locale images are selected for assignment analysis performed at 95% confidence interval. Pixel locations are assigned to the cytoplasm locale by exclusion.

The computer reads pixel intensities at each pixel location in the membrane and nucleus locale images, and compares them to threshold values. If neither of the intensity values are greater than the threshold values, the pixel location is assigned to the cytoplasm locale. If only the nuclear intensity or membrane intensity is greater than the threshold value, the computer assigns the pixel location to the above-threshold locale. If both intensities are higher than the thresholds, computer compares the ratio of the intensity values to one, and makes an assignment as follows:

$$\frac{\text{nuclear intensity}}{\text{membrane intensity}} > 1 \rightarrow \text{pixel location} = \text{nuclear locale}$$

$$\frac{\text{nuclear intensity}}{\text{membrane intensity}} < 1 \rightarrow \text{pixel location} = \text{membrane locale.}$$

$$\frac{\text{nuclear intensity}}{\text{membrane intensity}} = 1 \rightarrow \text{pixel location} = \text{unassigned}$$

Thus, if the nuclear intensity is greater than the membrane intensity, the computer assigns the pixel location to the nuclear locale. If the membrane intensity is greater than the nuclear intensity, the computer assigns the pixel location to the membrane locale. If the membrane intensity is equal to the nuclear intensity, the pixel location is unassigned. This repeats for the pixel locations.

Once all the pixel locations have been analyzed, the computer determines the amount of nuclear intensity incorrectly assigned to the membrane locale (i.e., nuclear to membrane spill-over), and vice versa. If the amount of nuclear intensity incorrectly assigned to the membrane channel is >5% of the total nuclear intensity, then the computer weights the nuclear intensity by a factor, w, and recalculates the ratio of weighted nuclear intensity to membrane intensity. This ratio is compared to one, and pixel locations are reassigned as follows:

$$\frac{w \times \text{nuclear intensity}}{\text{membrane intensity}} > 1 \rightarrow \text{pixel location} = \text{nuclear locale}$$

$$\frac{w \times \text{nuclear intensity}}{\text{membrane intensity}} < 1 \rightarrow \text{pixel location} = \text{membrane locale.}$$

$$\frac{w \times \text{nuclear intensity}}{\text{membrane intensity}} = 1 \rightarrow \text{pixel location} = \text{unassigned}$$

The computer again determines the amount of each locale incorrectly assigned. If this is still >5% the computer increases the value of w and reiterates the steps above. This continues until the amount of incorrectly assigned nuclear locale is <5%. The computer employs a similar technique to minimize the membrane-to-nuclear spillover.

The computer also calculates the area of the cytoplasmic (exclusion) locale and compares it to a predetermined value. By iterating the assignment process, the computer ensures that there is <5% cytoplasmic-to-nuclear or cytoplasmic-to-membrane, as determined based on the biology.

The computer then evaluates the amount of signal in each locale during a "signal assignment" process.

Following pixel assignment, the computer sums the signal in each locale. The computer reads the pixel intensity of the signal image (i.e., the image of the stain that selectively labels the cellular component), and adds together the signal intensity for pixel locations assigned to like subcellular compartments. The computer calculates a pixel intensity sum of a locale by the direct addition of the signal intensity of each pixel location assigned to that locale. The computer also calculates a sum of pixel intensity ratios by adding together the ratio of the signal intensity and the locale intensity for each pixel location.

The pixel intensity sum and pixel intensity ratio sum is then used in calculating one or more parameters. For example, the computer determines the relative percentage of signal falling within each of the compartments (e.g. 30% of the total signal is membranous, 20% is cytoplasmic, and 50% is nuclear). In another example, the computer expresses the amount of signal present relative to the size of a particular compartment (e.g. the signal intensity of pixels assigned to the membrane channel divided by the number of pixels assigned to the membrane channel). The user may select to have the computer evaluate other parameters of interest. For example, how much of the image area is covered by the mask, how much of the mask is covered by each locale, etc.

By implementing the pseudo-deconvolution algorithm (which limits the majority of extraneous pixel intensity) together with intensity area measurements (which further define the area of a particular sub-cellular locale), the computer is able to make highly accurate assignments of pixel locations sub-cellular locations.

In some embodiments, the computer performs additional steps to better utilize the dynamic range of the camera. This is achieved by redistributing the pixel intensities in an image across the dynamic range of the detector based on their relative intensities.

One form of redistribution is normalized redistribution, whereby the lower threshold (i.e., the pixel intensity of the background, determined during masking) is subtracted from all the pixels in the image, and any pixel with a resulting negative value is set to zero. Normalized redistribution is used for the signal channel as this redistribution preserves the scale from one sample to the next, allowing direct comparisons to be made between samples. This is performed either after masking the signal image.

Double-logarithmic redistribution sets all pixels in an image above 50% of the image's upper threshold (i.e., the value which only 50% of the pixels in the image have greater intensity) to the maximum intensity value (e.g., 255 for an 8-bit image). All pixels with intensity values below the lower threshold are set to 0, and all pixels with intensity values between the upper and lower thresholds are reassigned according to the formula:

$$I_{new} = \frac{\log(I_{old} - LT)}{I_{max}\log\left(\frac{1}{2}UT - LT\right)},$$

where $I_{new}$ refers to the new pixel intensity, $I_{old}$ refers to the old pixel intensity, LT and UT are the lower and 50% maximum thresholds, respectively, and $I_{max}$ is the maximum intensity value. Double-logarithmic redistribution is used for the locale channels, either after masking or after pseudo-deconvolution of these channels. Conceptually, it ensures that pixels in locale images that have intensities above the $50^{th}$ percentile are assigned to their locale during the assignment phase. Pixels with intensities below, but close to, the $50^{th}$ percentile are weighted more heavily and are more likely to be assigned to the locale than pixels that have intensities well below the $50^{th}$ percentile.

Other user-defined redistributions, such as linear redistributions or other equation-based redistributions, may be used in addition to the above-described examples.

Although the algorithms described above are with reference to analysis of tissue microarrays, they are not limited to studying only such arrays. The spotfinder algorithm may be used for identifying the location of any element comprising a collection and the RESA and PLACE algorithms may be used to localize and quantitate a biomarker within any imageable, cell containing sample, including tissue biopsies and cell containing fluid samples, such as blood, urine, spinal fluid, saliva, lymph, pleural fluid, peritoneal fluid and pericardial fluid.

Also, any optical or non-optical imaging device can be used, such as for example, upright or inverted optical microscopes, scanning confocal microscopes, cameras, scanning or tunneling electron microscopes, scanning probe microscopes, and imaging infrared detectors etc.

In the embodiments described above, the computer can include hardware, software, or a combination of both to control the other components of the system and to analyze the images to extract the desired information about the histospots and tissue microarrays. The analysis described above is implemented in computer programs using standard programming techniques. Such programs are designed to execute on programmable computers each comprising a processor, a data storage system (including memory and/or storage elements), at least one input device, at least one output device, such as a display or printer. The program code is applied to input data (e.g., stitched together images or image stacks) to perform the functions described herein and generate information (e.g., localization of signal), which is applied to one or more output devices. Each computer program can be implemented in a high-level procedural or object-oriented programming language, or an assembly or machine language. Each such computer program can be stored on a computer readable storage medium (e.g., CD ROM or magnetic diskette) that when read by a computer can cause the processor in the computer to perform the analysis described herein.

Figure 5:
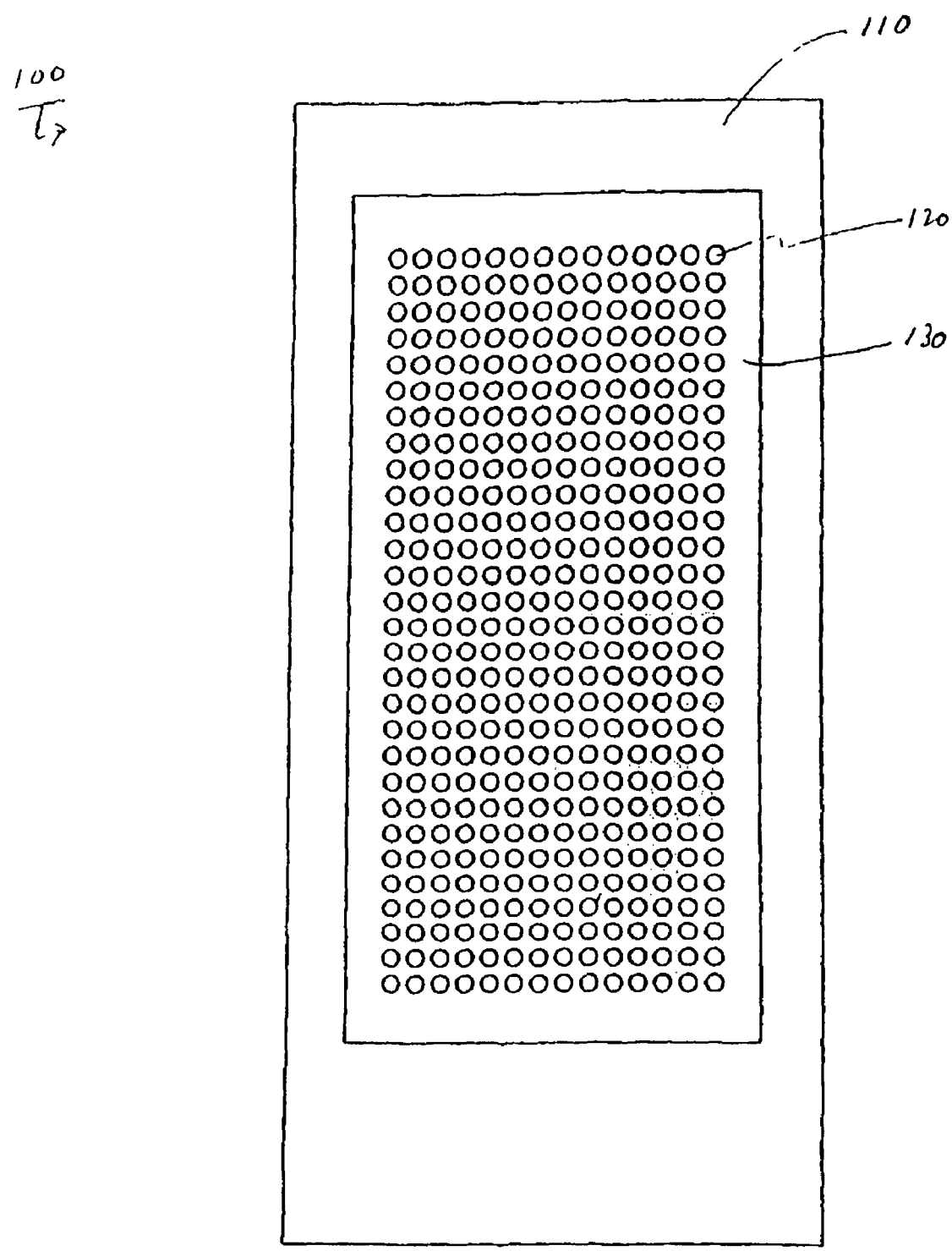
FIG. 5 shows a tissue microarray.

The following provides a detailed description of a specific embodiment of the preparation and analysis of tissue microarrays according to methods described herein, although similar steps could be performed with respect to any cell containing sample. Referring to FIG. 5, a tissue microarray 100 includes multiple samples of histospots 120 prepared from histocores embedded typically in a thin (e.g., about five microns) block of paraffin 130 at regular intervals, forming a series of rows and columns. Histospots (thin sections of histocores) 120 may be substantially disk-like in shape and will typically have the same thickness as the paraffin block 130 (i.e., about five microns) and a diameter of about 0.6 millimeters. Typically the centers of the histospots are spaced about a few tenths of a millimeter apart. Paraffin block 130 and histospots 120 may be mounted on a microscope slide 110. A tissue microarray 100 may include any number of histospots, typically on the order of several hundred to a few thousand.

Referring to FIG. 6, an optical microscopy station can be used to obtain an appropriate image of the tissue. Microscopy station 200 includes an inverted optical microscope 201 for imaging the tissue, and a computer 290 for analyzing the images. Optical microscope 201 includes a mount 210, housing a light source 220, a sample stage 240, an objective lens 250 and a CCD camera 270. A frame grabber in computer 290 acquires the images through CCD camera 270.

Optical microscope 201 also includes filter wheels 230 and 260, which house a series of dichroic filters. The filters in wheel 230 allow selection of the appropriate illumination spectra for standard or fluorescent microscopy. Filters in wheel 260 filter the transmitted light for isolation of spectral signatures in fluorescent microscopy. Sample stage 240 supports and appropriately positions tissue microarray 100. Sample stage 240 can be linearly translated in the x, y, and z directions (axes are shown). Sample stage 240 includes motors to enable automated translation. Computer 290 controls sample stage 240 translation by servo control of the motors.

A tissue microarray 100 can be imaged as follows: a user places the microarray on a sample stage 240. The user adjusts sample stage 240 so that the first (i.e., top-left) histospot is at the center of the field of view and focused on CCD camera 270. The objective lens 250 should be adjusted to the appropriate resolution, for example, a 0.6 millimeter histospot can be viewed at 10× magnification. Generally, the histospots correspond to areas of higher light intensity than the surrounding paraffin, as assessed through various means including signals derived from the visible light scattering of stained tissues, tissue autofluorescence or from a fluorescent tag. Computer 290 can acquire a low-resolution image (e.g. 64 pixel×64 pixel with 16 bin resolution) using computer software (Softworx 2.5, Applied Precision, Issaquah, Wash.) and an imaging platform (e.g., Deltavision). Computer 290 automatically translates sample stage 240 by an amount approximately equal to a field of view. The computer then acquires a second low-resolution image. This process is repeated until the computer has acquired images of the entire tissue microarray. Then, using commercially available software, the computer generates a composite image of the entire tissue microarray by stitching together the sequence of images like a patchwork.

Biological markers, which may be detected in accordance with the present invention include, but are not limited to any nucleic acids, proteins, peptides, lipids, carbohydrates or other components of a cell. Certain markers are characteristic of particular cells, while other markers have been identified as being associated with a particular disease or condition. Examples of known prognostic markers include enzymatic markers such as galactosyl transferase II, neuron specific enolase, proton ATPase-2, and acid phosphatase. Hormone or hormone receptor markers include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor.

Lymphoid markers include alpha-1-antichymotrypsin, alpha-1-antitrypsin, B cell marker, bcl-2, bcl-6, B lymphocyte antigen 36 kD, BM1 (myeloid marker), BM2 (myeloid marker), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage marker, muramidase (lysozyme), p80 anaplastic lymphoma kinase, plasma cell marker, secretory leukocyte protease inhibitor, T cell antigen receptor (JOVI 1), T cell antigen receptor (JOVI 3), terminal deoxynucleotidyl transferase, unclustered B cell marker.

Tumour markers include alpha fetoprotein, apolipoprotein D, BAG-1 (RAP46 protein), CA 19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma marker (HMB45), mesothelin, metallothionein, microphthalmia transcription factor (MITF), Muc-1 core glycoprotein. Muc-1 glycoprotein, Muc-2 glycoprotein, Muc-SAC glycoprotein, Muc-6 glycoprotein, mycloperoxidase, Myf-3 (Rhabdomyosarcoma marker), Myf-4 (Rhabdomyosarcoma marker), MyoD1 (Rhabdomyosarcoma marker), myoglobin, nm23 protein, placental alkaline phosphatase, prealbumin, prostate specific antigen, prostatic acid phosphatase, prostatic inhibin peptide, PTEN, renal cell carcinoma marker, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, von Willebrand factor.

Cell cycle associated markers include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p 16 protein, p27 protein, p34cdc2, p57 protein (Kip2), p105 protein, Stat 1 alpha, topoisomerase I, topoisomerase II alpha, topoisomerase III alpha, topoisomerase II beta.

Neural tissue and tumour markers include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma marker, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, scrotonin, SNAP-25, synapsin 1, synaptophysin, tau, tryptophan hydroxylase, tyrosine hydroxylase, ubiquitin.

Cluster differentiation markers include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD2S, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a. CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148. CDw149, CDw150, CD151, CD152, CD153, CD154, CD155, CD156, CD157, CD158a, CD158b, CD161, CD162, CD163, CD164, CD165, CD166, and TCR-zeta.

Other cellular markers include centromere protein-F (CENP-F), giantin, involucrin, lamin A&C [XB10], LAP-70, mucin, nuclear pore complex proteins, p180 lamellar body protein, ran, r, cathepsin D, Ps2 protein, Her2-neu, P53, S100, epithelial marker antigen (EMA), TdT, MB2, MB3, PCNA, and Ki67.

Cell containing samples may be stained using dyes or stains, or histochemicals, that directly react with the specific biomarkers or with various types of cells or subcellular compartments. Not all stains are compatible. Therefore the type of stains employed and their sequence of application should be well considered, but can be readily determined by one of skill in the art. Such histochemicals may be chromophores detectable by transmittance microscopy or fluorophores detectable by fluorescence microscopy. In general, a cell containing samples may be incubated with a solution comprising at least one histochemical, which will directly react with or bind to chemical groups of the target. Some histochemicals must be co-incubated with a mordant, or metal, in order to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes.

The following, non-limiting list provides exemplary chromophores that may be used as histological stains or counterstains and their target cells, subcellular compartments, or cellular components: Eosin (alkaline cellular components, cytoplasm), Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (which typically includes a mixture of Hematoxylin, Eosin Y, Orange G and Bismarck Brown mixture (overall cell morphology), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleoli differently), Aldehyde Fuchsin (elastin fibers), and Weigert stain (differentiates reticular and collagenous fibers). A comprehensive list of such stains, their description, and general use is given in R. D. Lillie, "Conn's Biological Stains", 8th ed., Williams and Wilkins Company, Baltimore, Md. (1969). Suitable mordants and compositions of the preceding are well-known to one of skill in the art.

The following, non-limiting list provides exemplary fluorescent histological stains and (heir target cells, subcellular compartments, or cellular components if applicable: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

A wide variety of proprietary fluorescent organelle-specific probes are available from Molecular Probes (Eugene, Oreg.), which include mitochondria-specific probes (MitoFluor and MitoTracker dyes), endoplasmic reticulum (ER) and Golgi probes (ER-Tracker and various ceramide conjugates), and lysosomal probes (LysoTracker dyes). These probes, as well as many nonproprietary fluorescent histochemicals, are available from and extensively described in the *Handbook of Fluorescent Probes and Research Products* $8^{th}$ Ed. (2001), available from Molecular Probes, Eugene, Oreg.

Each cell containing sample may be co-incubated with appropriate substrates for an enzyme that is a cellular component of interest and appropriate reagents that yield colored precipitates at the sites of enzyme activity. Such enzyme histochemical stains are specific for the particular target enzyme. Staining with enzyme histochemical stains may be used to define a subcellular component or a particular type of cell. Alternatively, enzyme histochemical stains may be used diagnostically to quantitate the amount of enzyme activity in cells. A wide variety of enzymatic substrates and detection assays are known and described in the art, and some selected methods are exemplified below.

Acid phosphatases may be detected through several methods. In the Gomori method for acid phophatase, a cell preparation is incubated with glycerophosphate and lead nitrate. The enzyme liberates phosphate, which combines with lead to produce lead phosphate, a colorless precipitate. The tissue is then immersed in a solution of ammonium sulfide, which reacts with lead phosphate to form lead sulfide, a black precipitate. Alternatively, cells may be incubated with a solution comprising pararosanilin-HCl, sodium nitrite, napthol ASBI phosphate (substrate), and veronal acetate buffer. This method produces a red precipitate in the areas of acid phosphatase activity. Owing to their characteristic content of acid phosphatase, lysosomes can be distinguished from other cytoplasmic granules and organelles through the use of this assay.

Dehydrogenases may be localized by incubating cells with an appropriate substrate for the species of dehydrogenase and tetrazole. The enzyme transfers hydrogen ions from the substrate to tetrazole, reducing tetrazole to formazan, a dark precipitate. For example, NADH dehydrogenase is a component of complex I of the respiratory chain and is localized predominantly to the mitochondria.

Other enzymes for which well-known staining techniques have been developed, and their primary cellular locations or activities, include but are not limited to the following: ATPases (muscle fibers), succinate dehydrogenases (mitochondria), cytochrome coxidases (mitochondria), phosphorylases (mitochondria), phosphofructokinases (mitochondria), acetyl cholinesterases (nerve cells), lactases (small intestine), leucine aminopeptidases (liver cells), myodenylate deaminases (muscle cells), NADH diaphorases (erythrocytes), and sucrases (small intestine).

Immunohistochemistry is among the most sensitive and specific histochemical techniques. Each histospot may be combined with a labeled binding composition comprising a specifically binding probe. Various labels may be employed, such as fluorophores, or enzymes which produce a product which absorbs light or fluoresces. A wide variety of labels are known which provide for strong signals in relation to a single binding event. Multiple probes used in the staining may be labeled with more than one distinguishable fluorescent label.

These color differences provide a way to identify the positions of specific probes. The method of preparing conjugates of fluorophores and proteins, such as antibodies, is extensively described in the literature and does not require exemplification here.

Although there are at least 120,000 commercially available antibodies, the following lists some exemplary primary antibodies known to specifically bind cellular components and which are presently employed as components in immunohistochemical stains used for research and, in limited cases, for diagnosis of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multidrug resistance), anti-CEA antibody (carcinoembryonic antigen), anti-retinoblastoma protein (Rb) antibody, anti-ras oneoprotein (p21) antibody, anti-Lewis Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD 31 antibody (angiogenesis marker), anti-CD33 antibody (myeloid cells, AML), anti-CD34 antibody (endothelial stem cells, stromal tumors), anti-CD35 antibody (dendritic cells), anti-CD 38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), and anti-Tn-antigen antibody (colon carcinoma, adenocarcinomas, and pancreatic cancer).

Fluorophores that may be conjugated to a primary antibody include but are not limited to Fluorescein, Rhodamine, Texas Red, Cy2, Cy3, Cy5, VECTOR Red, ELF™ (Enzyme-Labeled Fluorescence), Cy0, Cy0.5, Cy1.5, Cy1.5, Cy3, Cy3.5, Cy5, Cy7, Fluor X, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine and Tryptophan. A wide variety of other fluorescent probes are available from and/or extensively described in the *Handbook of Fluorescent Probes and Research Products* $8^{th}$ Ed. (2001), available from Molecular Probes, Eugene, Oreg., as well as many other manufacturers.

Further amplification of the signal can be achieved by using combinations of specific binding members, such as antibodies and anti-antibodies, where the anti-antibodies bind to a conserved region of the target antibody probe, particularly where the antibodies are from different species. Alternatively specific binding ligand-receptor pairs, such as biotin-streptavidin, may be used, where the primary antibody is conjugated to one member of the pair and the other member is labeled with a detectable probe. Thus, one effectively builds a sandwich of binding members, where the first binding member binds to the cellular component and serves to provide for secondary binding, where the secondary binding member may or may not include a label, which may further provide for tertiary binding where the tertiary binding member will provide a label.

The secondary antibody, avidin, strepavidin or biotin are each independently labeled with a detectable moiety, which can be an enzyme directing a colorimetric reaction of a substrate having a substantially non-soluble color reaction product, a fluorescent dye (stain), a luminescent dye or a non-fluorescent dye. Examples concerning each of these options are listed below.

In principle, any enzyme that (i) can be conjugated to or bind indirectly to (e.g., via conjugated avidin, strepavidin, biotin, secondary antibody) a primary antibody, and (ii) uses a soluble substrate to provide an insoluble product (precipitate) could be used.

The enzyme employed can be, for example, alkaline phosphatase, horseradish peroxidase, beta-galactosidase and/or glucose oxidase; and the substrate can respectively be an alkaline phosphatase, horseradish peroxidase, beta.-galactosidase or glucose oxidase substrate.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5'Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitrophenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan which forms the color precipitate.

Beta-galactosidase substrates, include, but are not limited to, 5-bromo-4-chloro-3-indoyl beta-D-galactopyranoside (X-gal, blue precipitate). The precipitates associated with each of the substrates listed have unique detectable spectral signatures (components).

The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and Ca.sup.++, having a luminescencing product.

The following references, which are incorporated herein provide additional examples. J. M Elias (1990) Immunohistopathology: A practical approach to diagnosis. ASCP Press (American Society of Clinical Pathologists), Chicago; J. F. MeGinty, F. E. Bloom (1983) *Double immunostaining reveals distinctions among opioid peptidergic neurons in the medial basal hypothalamus*. Brain Res. 278: 145-153; and T. Jowett (1997) *Tissue In situ Hybridization: Methods in Animal Development*. John Wiley & Sons, Inc., New York; J Histochem Cytochem 1997 December 45(12):1629-1641.

Cellular preparations may be subjected to in-situ hybridization (ISH). In general, a nucleic acid sequence probe is synthesized and labeled with either a fluorescent probe or one member of a ligand:receptor pair, such as biotin/avidin, labeled with a detectable moiety. Exemplary probes and moieties are described in the preceding section. The sequence probe is complementary to a target nucleotide sequence in the cell. Each cell or cellular compartment containing the target nucleotide sequence may bind the labeled probe. Probes used in the analysis may be either DNA or RNA oligonucleotides or polynucleotides and may contain not only naturally occurring nucleotides but their analogs such as dioxygenin dCTP, biotin dCTP 7-azaguanosine, azidothymidine, inosine, or uridine. Other useful probes include peptide probes and analogues thereof, branched gene DNA, peptidomimetics, peptide nucleic acids, and/or antibodies. Probes should have sufficient complementarity to the target nucleic acid sequence of interest so that stable and specific binding occurs between the target nucleic acid sequence and the probe. The degree of homology required for stable hybridization varies with the stringency of the hybridization. Conventional methodologies for ISH, hybridization and probe selection are described in Leitch, et al. *In Situ Hybridization: a practical guide*, Oxford BIOS Scientific Publishers, Microscopy Handbooks v. 27 (1994); and Sambrook, J., Fritsch, E. F., Maniatis, T., *Molecular Cloning: A Laboratory Manual*, Cold Spring Harbor Press (1989).

The present invention is further illustrated by the following examples, which should not be construed as limiting in any way. The contents of all cited references are hereby expressly incorporated by reference.

EXAMPLE 1

Construction of Tissue Microarrays for a Survival Analysis of the Estrogen Receptor (ER) and HER2/neu and for Analysis of Nuclear Associated Beta-Catenin Tissue microarray design: Paraffin-embedded formalin-fixed specimens from 345 cases of node-positive invasive breast carcinoma were identified. Areas of invasive carcinoma, away from in situ lesions and normal epithelium, were identified and three 0.6 cm punch "biopsy" cores were taken from separate areas. Each core was arrayed into a separate recipient block, and five-micron thick sections were cut and processed as previously described (Konenen, J. et al., Tissue microarrays for high-throughput molecular profiling of tumor specimens, (1987) *Nat. Med.* 4:844-7). Similarly, 310 cases of colon carcinoma were obtained and arrayed, as previously described (Chung, G. G. et al., *Clin. Cancer Res.* (In Press)).

Immunohistochemistry: Pre-cut paraffin-coated tissue microarray slides were deparaffinized and antigen-retrieved by pressure-cooking (Katoh, A. K. et al., (1997) *Biotech Histochem. F*2:291-8). Slides were stained with antibodies to one of three target antigens: monoclonal anti-E.R. (mouse, Dako Corporation, Carpinteria, Calif.), polyclonal anti-HER2/neu (rabbit, Dako Corp.), monoclonal (mouse clone 14, BD Transduction Labs, San Diego Calif.) anti-beta-catenin, or polyclonal rabbit anti-betacatenin. Primaries were incubated overnight it 4° C. A corresponding goat antimouse or anti-rabbit secondary antibody conjugated to a horseradish peroxidase decorated dextran-polymer backbone was then applied for 1 hr (Envision, DAKO Corp.). Target antigens were either visualized with a visible light chromagen (Diaminobenzidine, DAKO) for visual analysis, or a fluorescent chromagen (Cy-5-tyramide, NEN Life Science Products, Boston, Mass.). Slides designated for automated analysis were counterstained with DAPI for visualization of nuclei, and either polyclonal rabbit anticytokeratin (Zymed, So. San Francisco, Calif.) or rabbit anti-alpha-catenin (?) to distinguish between tumor cells and stroma as well as to visualize the cell membrane. In many cases, exponentially subtracted images of histospots stained with anti-cytokeratin provided an acceptable marker for the cell membrane due to the submembranous coalescence of cytokeratin in tumor cells. These antibodies were visualized using either Cy3- or Alexa 488-conjugated goat anti-mouse or anti-rabbit secondary antibodies (Amersham, Piscataway, N.J. and Molecular Probes, Eugene, Oreg.). Slides designated for visual inspection were counterstained with ammonium hydroxide acidified hematoxylin. Manual examination of microarrays for E.R., HER2/neu, and beta-catenin levels has been previously described (Snead, D. R. et al., (1993) *Histopathology* 23:233-8).

Image analysis: Images of microarrays were obtained using a Deltavision platform and software (SoftWorx 2.5)

(Applied Precision, Issaquah, Wash.), with an attached water-cooled Photometrics series 300 camera through a 10× Nikon Super-Fluor lens on a TE200 inverted fluorescent microscope with automated X, Y, Z stage movement. Low power images of microarrays were stitched together using multiple (~1500) low resolution images of the microarray (64×64 pixel). These images were analyzed by software algorithms described herein to determine the location of each. Subsequently, monochromatic, high resolution (1024×1024 pixel) images were obtained of each, both in the plane of focus and 8 microns below it. Image pairs for each fluorescent dye were obtained. Images were analyzed using additional algorithms as follows, in brief. Regions of interest (tumor) were identified using a mask derived from a ubiquitously-expressed epithelial-specific antigen (either cytokeratin or alpha-catenin). Images of fluorescently-tagged membrane and nuclear compartments were exponentially subtracted until a set amount of image intensity remained. Images were then combined so that there was minimal overlap of signal from one compartment to the next. Pixels in which a significant degree of overlap was present were negated from further analysis. The pixel intensity of exponentially subtracted images of the target antigen were assigned to one of three compartments: nuclear, membrane, or non-nuclear non-membrane (cytoplasm). Target intensities were analyzed as described below. For E.R. only nuclear-localized signal was used, for HER2/neu only membrane-localized signal was analyzed. For beta-catenin total signal, the ratio of nuclear to membrane signal, and the ratio of nuclear to total signal was analyzed.

Data analysis: staining scores from the breast cancers represent the averaged (for ER) or maximized (for HER2/neu) results from two scorable histospots. Subsequent studies revealed that analysis of a single histospot could provide significant statistical power to judge outcomes, so that staining scores from the colon cancer array represent the result of only one histospot. Overall survival analysis was assessed using Kaplan-Meier analysis and the Mantel-Cox log rank score for assessing statistical significance. Relative risk was assessed using the univariate Coxproportional hazards model. Analyses were performed using Statview 5.0.1 (SAS Institute, Cary N.C.).

What is claimed is:

1. A method for identifying a location for each of a plurality of histospots in an image of a stained tissue microarray comprising:
    obtaining an image using an optical imaging device; and
    using a programmable computer to perform the steps of:
        a) removing from the image any of the histospots that are debris and/or are fused histospots;
        b) applying a virtual mask that has a size and shape characteristic of a histospot which does not constitute a fused histospot and/or debris within the plurality of spots so as to cover an area of the image having a pixel intensity area which is higher than the pixel intensity area anywhere else in the image;
        c) temporarily setting the intensity of the image in the area under the mask to zero;
        d) repeating steps (b) and (c) until no area is identified having a sufficient intensity to qualify as a histospot;
        e) identifying a reference point within each of the histospots; and
        f) connecting the reference point within each of the spots to either a nearest neighboring histospot or to edge of the image;
    thereby identifying the location for each of the plurality of histospots in the image.

2. The method of claim 1, wherein the plurality of histospots is present in a tissue microarray.

3. The method of claim 2, wherein the tissue microarray is fixed.

4. The method of claim 3, wherein the tissue microarray is paraffin embedded.

5. The method of claim 3, wherein the stained tissue comprises a fluorophore.

6. The method of claim 1 wherein the imaging device is a microscope.

7. The method of claim 6 in which the microscope is an upright or inverted optical microscope.

8. The method of claim 6 in which the microscope is a fluorescent microscope.

* * * * *